(12) United States Patent
Vitaris et al.

(10) Patent No.: US 9,517,164 B2
(45) Date of Patent: Dec. 13, 2016

(54) WOUND DRESSING WITH ADVANCED FLUID HANDLING

(75) Inventors: Ronald F. Vitaris, Worcester, MA (US); Kevin M. Corley, Reading, MA (US)

(73) Assignee: Covidien LP, Mansfield, MA (US)

( * ) Notice: Subject to any disclaimer, the term of this patent is extended or adjusted under 35 U.S.C. 154(b) by 421 days.

(21) Appl. No.: 12/894,584

(22) Filed: Sep. 30, 2010

(65) Prior Publication Data
US 2012/0083723 A1   Apr. 5, 2012

(51) Int. Cl.
*A61F 13/00* (2006.01)
*A61F 13/02* (2006.01)

(52) U.S. Cl.
CPC ....... *A61F 13/0203* (2013.01); *A61F 13/0276* (2013.01)

(58) Field of Classification Search
USPC ...... 602/41–58; 128/888–889; 424/443–449; 604/304–308
See application file for complete search history.

(56) References Cited

U.S. PATENT DOCUMENTS

| | | | | |
|---|---|---|---|---|
| 4,649,909 A | * | 3/1987 | Thompson | 602/42 |
| 5,056,510 A | * | 10/1991 | Gilman | 602/52 |
| 5,086,764 A | * | 2/1992 | Gilman | 602/42 |
| 5,106,362 A | * | 4/1992 | Gilman | 602/47 |
| 5,167,613 A | | 12/1992 | Karami et al. | |
| 5,409,472 A | * | 4/1995 | Rawlings et al. | 604/307 |
| 5,447,492 A | * | 9/1995 | Cartmell et al. | 602/58 |
| 5,556,375 A | * | 9/1996 | Ewall | 602/58 |
| 5,593,395 A | | 1/1997 | Martz | |
| 5,607,388 A | * | 3/1997 | Ewall | 602/58 |
| 5,629,014 A | | 5/1997 | Kwiatek et al. | |
| 6,066,773 A | | 5/2000 | Freeman | |
| 6,420,624 B1 | | 7/2002 | Kawase | |
| 6,447,497 B1 | * | 9/2002 | Olson | 604/389 |
| 6,566,575 B1 | | 5/2003 | Stickels et al. | |
| 6,787,682 B2 | * | 9/2004 | Gilman | 602/58 |

(Continued)

FOREIGN PATENT DOCUMENTS

| | | |
|---|---|---|
| WO | WO 02/05737 | 1/2002 |
| WO | WO 2006/089551 | 8/2006 |
| WO | WO 2008/043364 A1 | 4/2008 |

OTHER PUBLICATIONS

Examination Report dated Jun. 4, 2013 from corresponding Canadian Application No. 2,753,086 (3 pgs.).

(Continued)

*Primary Examiner* — Ophelia A Hawthorne

(57) ABSTRACT

A wound dressing for managing wound fluids includes a porous contact layer for positioning adjacent a wound. An internal open window extends through the contact layer exposing a distal side of an absorbent member. The absorbent member is disposed in a superimposed relation to the window of the contact layer and is dimensioned to extend laterally beyond the window such that a portion of the absorbent member overlaps and is secured to the contact layer. A drape layer is disposed on a proximal side of the absorbent member, and is adhesively coated to fasten the drape layer to the absorbent member. A cover layer disposed over the drape layer defines an internal open window such that the open window is adjacent the absorbent member. A distal side of the cover layer is adhesively coated to secure the cover layer to the contact layer.

20 Claims, 3 Drawing Sheets

(56) References Cited

U.S. PATENT DOCUMENTS

2005/0249791 A1* 11/2005 Hobbs et al. .................. 424/443
2006/0173434 A1* 8/2006 Zoromski et al. ............. 604/374
2008/0171958 A1* 7/2008 Gundersen ..................... 602/56

OTHER PUBLICATIONS

Examination Report issued by the Australian Intellectual Property Office on Jul. 6, 2012 in counterpart Australian Patent Application No. 2011226984 (3 pgs.).

* cited by examiner

WOUND DRESSING WITH ADVANCED FLUID HANDLING

BACKGROUND

1. Technical Field

The present disclosure relates generally to wound dressings. In particular, the disclosure relates to a wound dressing adapted for receiving fluids that exude from a wound, and for directing and distributing the fluids within the dressing to promote healing of the wound.

2. Background of Related Art

Various techniques to promote healing of a wound involve covering the wound with a bandage or dressing. The dressing typically provides a barrier that inhibits bacterial migration from the ambient environment into the wound. Some dressings are equipped to absorb or receive "wound exudates," e.g., the fluid produced by the body that tends to accumulate in a wound. Historically, such dressings have included an absorbent material attached to an adhesive backing layer that provides a margin around the absorbent material. Thus the backing layer may be employed to adhesively seal the dressing to the skin around the wound. In use, these dressings may remain in place to receive and maintain the exudates in the absorbent material for several days. Since wound exudates typically includes water, the exudates maintained may serve to promote a moist wound environment, which may be particularly beneficial for dermal burns, pressure ulcers, incised wounds, or similar ailments.

As a wound dressing receives exudates, the absorbent material may tend to swell and distort the shape of the dressing. This distortion may undermine the effectiveness of the bacterial barrier of the wound dressing by reducing the dressing's ability to adhere to the skin. Additionally the distortion may permit moisture that is drawn away from the wound by the absorbent material to settle in the periwound area, e.g. the area of skin laterally surrounding the wound. Moisture in the periwound area may induce further tissue deterioration.

SUMMARY

The present disclosure describes a wound dressing suitable for managing fluids such as wound exudates. The dressing includes a porous contact layer for positioning adjacent a wound. The porous contact layer defines a distal wound-facing surface, an opposed proximal surface, and an internal open window extending therethrough. An absorbent member is disposed in superimposed relation to the window of the contact layer, and is dimensioned to extend laterally beyond the window such that a portion of the absorbent member overlaps and is secured to the proximal surface of the contact layer. A drape layer is disposed on a proximal side of the absorbent member. A distal side of the drape layer is adhesively coated to fasten the drape layer to the absorbent member. A cover layer defines an internal open window, and is disposed over the drape layer such that the open window is adjacent the absorbent member. A distal side of the cover layer is adhesively coated to secure the cover layer to the contact layer.

At least about 50% of the surface area of a distal side of the absorbent member may be exposed to a distal side of the dressing through the internal open window of the contact layer. In some embodiments, at least about 85% of the surface area of the distal side of the absorbent member is exposed through the internal open window of the contact layer. The absorbent member may define a generally rectangular shape, and the internal open window of the contact layer may define a generally circular or oval shape. The absorbent member may be constructed of an open-celled polyurethane foam.

The contact layer may include a layer of a cross linked, acrylic-based construction adhesive on a proximal side thereof that adherers the absorbent member to the contact layer. The distal side of the drape layer may be adhesively coated with a patterned coating of the construction adhesive.

The porous contact layer may include a plurality of perforations extending therethrough that exhibit a diameter in the range of about 200 to about 1000 microns, and are spaced such that the contact layer exhibits a perforation density in the range of about 50 to about 300 perforations per square inch. The perforations may exhibit a diameter of about 500 microns, and the perforation density of the contact layer may be about 85 microns per square inch. The contact layer may be constructed as a composite including a thin film substrate component that is coated on a distal side with a pressure sensitive, wound-side adhesive component, and coated on a proximal side with a construction adhesive component. The plurality of perforations may extend through each of the component layers of the contact layer.

According to another aspect of the disclosure, a wound dressing includes an absorbent member defining a distal wound-facing surface and an opposed proximal surface. The distal wound facing surface defines a surface area. A porous contact layer defines an internal open window extending therethrough. The porous contact layer includes a thin film membrane having a pressure sensitive, wound-side adhesive on a distal side thereof and a continuous coating of a construction adhesive on a proximal side thereof. The proximal side of the porous contact layer is adhered to the distal wound facing surface of the absorbent member such that at least about 50 percent of the surface area of the distal side of the absorbent member is exposed to a distal side of the wound dressing through the internal open window. A backing layer includes a patterned coating of the construction adhesive on a distal side thereof, and is adhered to the proximal side of the absorbent member by the patterned coating of the construction adhesive.

The patterned coating of the construction adhesive may be in the range of about 0.4 to about 0.6 grams of adhesive per 100 square inches of surface area of the backing layer. The backing layer may be constructed as a composite including a drape layer adhered to the absorbent member by the patterned coating of the construction adhesive on a distal side thereof, and a cover layer defining an internal open window. The cover layer may be adhered to a proximal side of the drape layer by a continuous or patterned coating of the construction adhesive. An outer edge of the cover layer may be coincident with an outer edge of the porous contact layer, and an outer edge of the drape layer may be coincident with an outer edge of the absorbent member.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
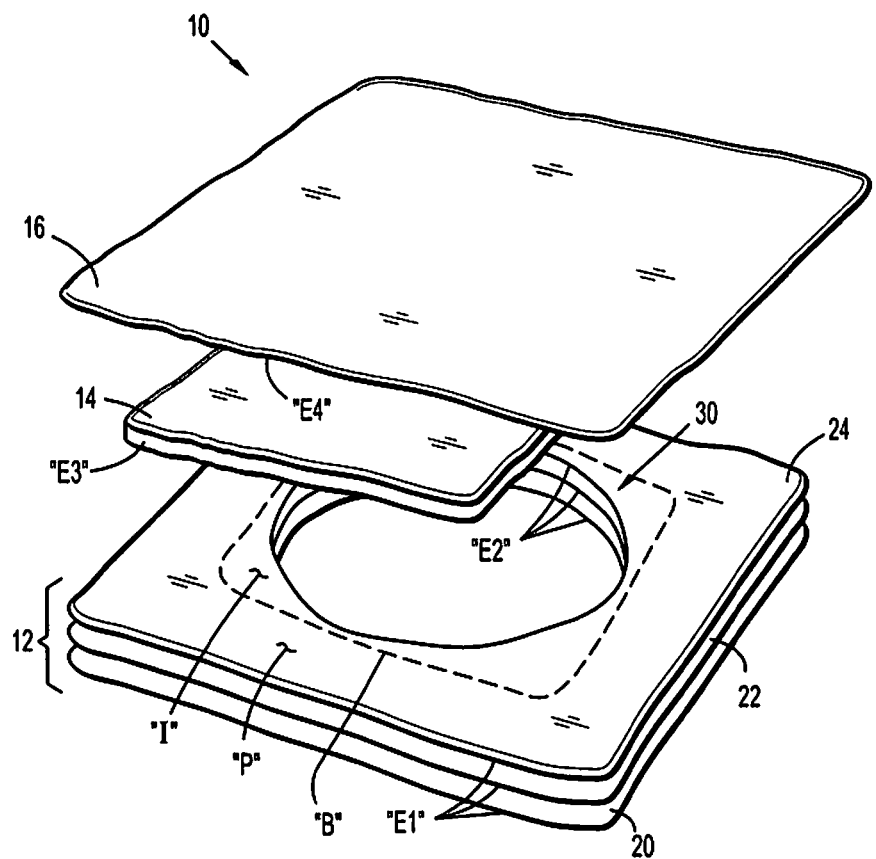
FIG. 1 is an exploded perspective view of a wound dressing including a backing layer, an absorbent member and a composite contact layer in accordance with an embodiment of the present disclosure.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Referring initially to FIG. 1, a wound dressing 10 includes a composite contact layer 12, an intermediate absorbent member 14 and a backing layer 16. These components 12, 14, 16 are superimposed and adhered with one another to form the unitary dressing 10. The contact layer 12 is disposed on a distal or wound-facing side of the dressing 10, and is adapted for contact with a patient to secure the dressing 10 over a wound "W" (see FIG. 4). The backing layer 16 is disposed on a proximal, or non-wound facing side of the dressing 10, and extends laterally beyond the absorbent member 14. As described in greater detail below, the backing layer 16 may be adhesively coupled to a perimeter of the contact layer 12 such that the absorbent member 14 is sandwiched between the attachment and backing layers 12, 16.

The composite contact layer 12 is constructed of three distinct component layers including a wound-side adhesive layer 20, a membrane or thin film layer 22, and a construction adhesive layer 24. The wound-side adhesive layer 20 is suitable for direct contact with a wound or the skin of a patient, and defines a distal surface of the contact layer 12. A pressure sensitive, acrylic copolymer adhesive such Gelva® GMS 2495 provided by Cytec Industries of Woodland Park, N.J. may be suitable for use as the wound side-adhesive. Other suitable adhesives for the wound-side adhesive layer 20 include Gelva® GMS 737, silicone adhesives, and any other commercially available medical adhesives. The film layer 22 provides a substrate to which the adhesive layers 20, 24 may be adhered. An extensible, 1.0 mm thermoplastic urethane (TPU) film such as the commercially available Vacuflex film 18411 manufactured by OMNIFLEX of Greenfield, Mass. may serve as the film layer 22. Any thermoplastic film that can be perforated or otherwise made porous may be suitable for the construction of the film layer 22. The construction adhesive layer 24 defines a proximal surface of the contact layer 12 and may be constructed of a continuous coating of an acrylic copolymer adhesive such Gelva® GMS 3101-03 provided Cytec Industries.

The three component layers 20, 22 and 24 of the composite contact layer 12 are coextensive in that each of the component layers 20, 22 and 24 share an outer lateral edge "E1" and an inner lateral edge "E2". Laterally within the inner edge "E2", the contact layer 12 defines an internal open distal window such as fluid access opening 30 extending through the contact layer 12. The fluid access opening 30 is central to the contact layer 12, as well as central to the dressing 10. The shape of the central fluid access opening 30 may be generally round or oval as depicted, although alternative configurations and shapes, e.g., rectangular, may also be suitable.

A distal side of the absorbent member 14 is superimposed with and secured to the contact layer 12 by the construction adhesive layer 24 at a laterally interior portion "I" of the dressing 10. The interior portion "I" circumscribes the fluid access opening 30, and defines a boundary "B" that is coincident with an outer lateral edge "E3" of the absorbent member 14. Thus, the location of the boundary "B" and the size of the interior portion "I" are both defined by the lateral extent of the absorbent member 14. Only a fraction of the surface area of the distal side of the absorbent member 14 overlaps the construction adhesive layer 24. For example, about 50% or less of the surface area may overlap the construction adhesive layer 24 such that 50% or more surface area of the distal side of the absorbent member 14 is exposed to a distal side of the dressing through the fluid access opening 30. In some embodiments, about 15% of the surface area overlaps, while about 85% of the surface area of the distal side of the absorbent member 14 is exposed through the fluid access opening 30. The portion of the absorbent member 14 exposed through the fluid access opening 30 is substantially devoid of any adhesive.

The absorbent member 14 is intended to allow wound dressing 12 to absorb, capture, or transport wound exudates, and may be constructed of materials such as non-woven gauze, reticulated foam, or alginate fibers. In one embodiment, the absorbent member 14 may include a generally rectangular pad of Covidien™ AMD Antimicrobial Foam dressing. The Covidien™ AMD Foam dressing is polyurethane-based foam including the antiseptic agent polyhexamethylene biguanide (PHMB). A microstructured open-celled surface on the foam pad promotes absorption of exudates, and the added PHMB attacks bacteria on and within the dressing 10. The generally rectangular shape of the absorbent member 14 facilitates adhesion of the absorbent member to the contact layer 12 when the fluid access opening 30 defines a generally circular or oval shape.

A distal side of the backing layer 16 is coupled to the absorbent member 14, and is also coupled to a perimeter region "P" of the dressing 10 by the construction adhesive layer 24. The perimeter region "P" extends laterally between the boundary "B" and the outer edge "E1" of the contact layer 12. An outer edge "E4" of the backing layer 16 may be coincident with the outer edge "E1" of the contact layer 12. The backing layer 16 may be constructed of a moisture vapor permeable membrane to promote the exchange of oxygen and moisture between the wound "W" and the ambient atmosphere. Membranes that provide a sufficient moisture vapor transmission rate (MVTR) include the transparent membranes sold under the trade names NOVOTEX AB5454, and also POLYSKIN®II by Tyco Healthcare Group LP (d/b/a Covidien), for example. A thin, tinted urethane film that promotes moisture vapor transmission therethrough may also be suitable for use as the backing layer 16. Higher rates of moisture vapor transmission between have been demonstrated to generally promote wound healing.

Figure 2:
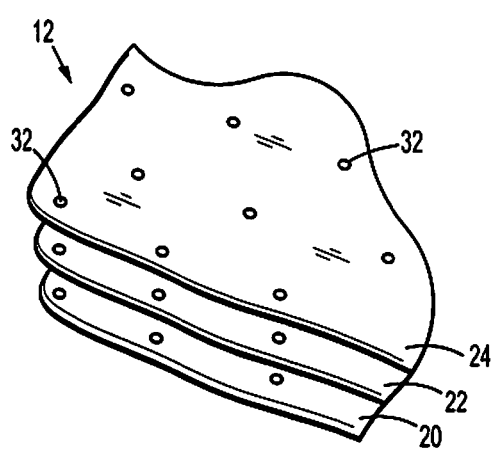
FIG. 2 is an enlarged perspective view of a corner portion of the composite contact layer of FIG. 1.

Referring now to FIG. 2, the contact layer 12 is porous to permit the transmission of wound fluids and moisture vapor therethrough. The contact layer 12 includes a plurality of perforations 32 extending through each of the component layers 20, 22 and 24. In the embodiment depicted in FIG. 2, the perforations 32 provide the porosity to the contact layer 32. Other embodiments are contemplated in which other structures such as a non-woven web or fabric (not shown) provides the porosity to the contact layer 32, and any type of porous membrane may also be suitable. The perforations 32 are generally circular in shape, and have a diameter in the range of about 200 to about 1000 microns. The perforations are spaced such that the contact layer 12 exhibits a perforation density in the range of about 50 to about 300 perforations 32 per square inch. In some embodiments, the perforations 32 exhibit a diameter of about 500 microns, and the perforation density of the contact layer 12 is about 85 microns per square inch. The perforations 32 permit transmission of wound exudates through the contact layer 12, and promote moisture vapor transmission through the dressing 10, particularly at the perimeter region "P" (FIG. 1) of the dressing 10.

Figure 3:
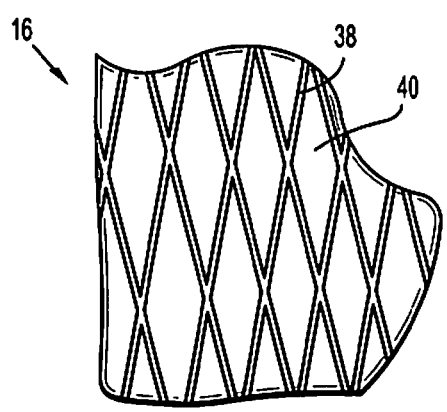
FIG. 3 is a distal or a wound-facing side view of the backing layer of FIG. 1.

Referring now to FIG. 3, the distal side of the backing layer 16 includes a patterned adhesive coating 38 disposed thereon. The adhesive coating 38 may be constructed of the same adhesive as the construction adhesive layer 24, e.g. the acrylic based Gelva® GMS 3101-03 adhesive discussed above. The patterned adhesive coating 38 is applied such that adhesive free areas 40 of the backing layer 16 form stretched or elongated diamond shapes. Alternatively, generally round, square or any other shape or pattern (not shown) of adhesive free areas on the backing layer 16 may be employed. The adhesive free areas 40 promote breathability and moisture vapor transmission through the backing layer 16. The adhesive coating 38 is relatively light, e.g. in the range of about 0.4 to about 0.6 grams of adhesive per 100 square inches of surface area. The light adhesive coating facilitates a controlled detachment of the backing layer 16 from the absorbent member 14 as described below with reference to FIG. 5.

When the wound dressing 10 is assembled, the continuous construction adhesive layer 24 and the patterned adhesive coating 38 adhere the various layers 12, 14, 16 of the wound dressing 10 to one another. The shear strength of the adhesive bond generated between the layers 12, 14 and 16 may be enhanced by subjecting the dressing 10 to a radiation sterilization procedure such as electron beam, X-ray or gamma radiation. The acrylic based construction adhesive cross links when exposed to radiation, and thus the shear strength is enhanced. The shear strength of the adhesive bond generated generally increases with radiation dosage. The enhanced shear strength enables the adhesive to become more resistant to de-bonding forces applied in a lateral direction. Lateral de-bonding forces may be generated by swelling of the absorbent member 14 as exudates are absorbed as discussed below with reference to FIG. 5. As discussed below, the enhanced shear strength of the construction adhesive discourages swelling of the absorbent member 14 in the lateral direction and promotes swelling of the absorbent member 12 in a vertical direction.

Figure 4:
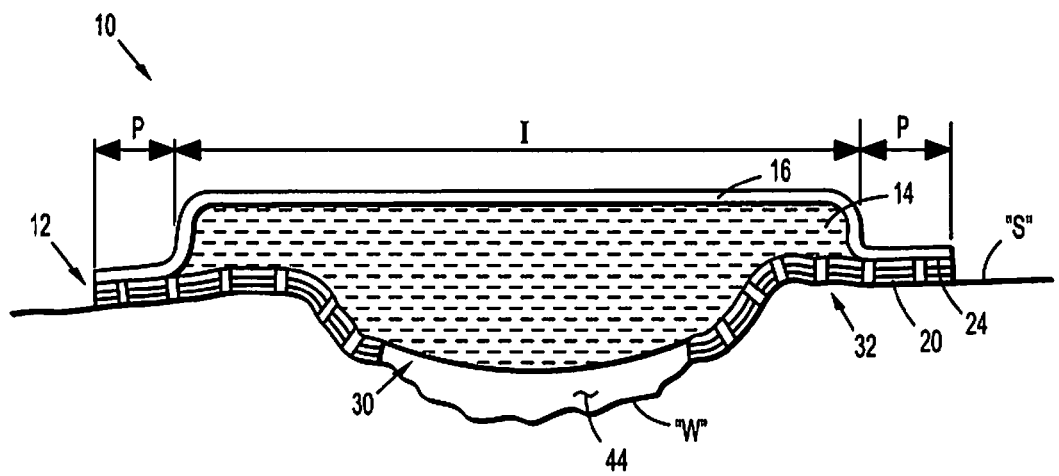
FIG. 4 is a cross-sectional view of the wound dressing of FIG. 1 assembled over a wound in an initial configuration prior to the receipt of wound exudates into the absorbent member.

Referring now to FIG. 4, the wound dressing 10 is depicted in an initial configuration as applied over a wound "W" prior to the receipt of wound exudates into the absorbent member 14. The wound-side adhesive layer 20 of the composite contact layer 12 adheres the dressing 10 to the skin "S". A portion of the composite contact layer 12 may extend laterally into the wound "W" as depicted, or alternatively, the fluid access opening 30 may be dimensioned to circumscribe the entire wound "W". The continuously coated construction adhesive layer 24 forms a sturdy bond between the backing layer 16 and the contact layer 12. The absorbent member 14 is laterally constrained within the interior region "I" of the dressing 10 by the bond generated between the backing layer 16 and the contact layer 12 in the perimeter region "P". The patterned coating 38 (FIG. 3) on the distal, wound-facing side of the backing layer 16 maintains the absorbent member 14 in intimate contact with the backing layer 16.

In the initial configuration, a void 44 may be established between the absorbent member 14 and the wound "W". The void 44 provides an area into which the absorbent absorbent member 14 may swell as exudates are absorbed. Unconstrained, the absorbent member 14 may have a tendency to swell uniformly in every direction. However, as assembled in the wound dressing 10, the swelling of the absorbent member 14 is constrained by the backing layer 16 and the contact layer 12. The fluid access opening 30 permits the absorbent member 14 to migrate or swell unobstructed, primarily in a vertical direction into the void 44.

Figure 5:
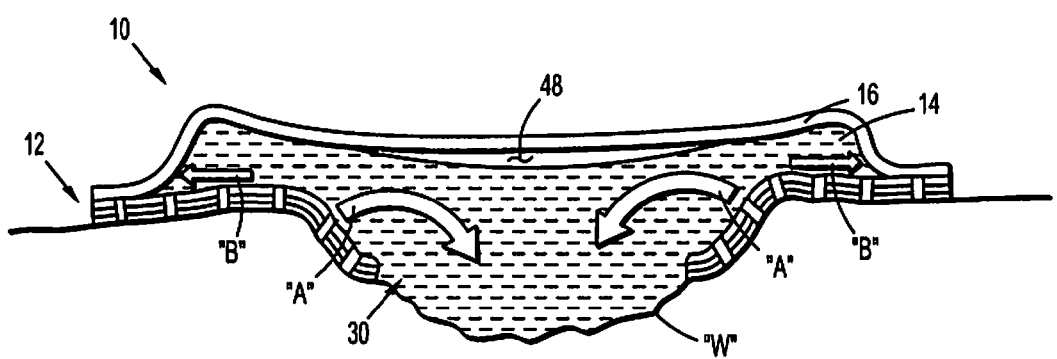
FIG. 5 is a cross-sectional view of the wound dressing of FIG. 1 assembled over the wound in a second configuration subsequent to the receipt of wound exudates into the absorbent member.

Referring now to FIG. 5, the wound dressing 10 is depicted in a second configuration wherein wound exudates have been received into the absorbent member 14. As the wound "W" produces exudates, the exudates are directed through the perforations 32 in the contact layer 12, and/or are directly received into the absorbent member 14. As indicated by arrows "A", the exudates move into a central area of the dressing 10 as the absorbent member 14 swells. The absorbent member 14 swells primarily in a vertical direction, and moves into the area previously occupied by the void 44 (FIG. 4). The swelling occurs primarily in the vertical direction since the force required for swelling in any other constrained direction is significantly greater than the force required for swelling in the unconstrained direction through the fluid access opening 30. The swelling draws the absorbent member 14 into intimate contact with the wound "W", and thus, maintains the wound "W" in a moist condition.

The absorbent member 14 also swells in a lateral direction as indicated by arrows "B". The lateral swelling stretches the absorbent member 14 laterally outward, which generates a buckling force in the absorbent member 14. The bucking force induces the central regions of the absorbent member 14 to move in the vertical direction, and assists in the movement of the absorbent member 14 through the fluid access opening 30. This swelling of the absorbent member 14 draws backing layer 16 toward the wound "W". A dimple or depression forms in backing layer 16 that begins in the central region of the dressing 10 and expands laterally outward as the absorbent member 14 becomes saturated with exudates. The patterned adhesive coating 38 (FIG. 3) is sufficiently light to permit separation of backing layer 16 from the absorbent member 14 such that a proximal reservoir 48 develops in the dressing 10. The proximal reservoir 48 provides a space into additional vertical swelling may occur, or into which exudates may flow. Thus, the configuration of the dressing 10 permits the dressing 10 to remain attached to the skin even after the absorbent member 14 is saturated.

Exudates in the proximal reservoir 48 exchange moisture vapor through the backing layer 16 at a higher rate than the portions of a moist pad layer attached to the backing layer 16. Also, since the proximal reservoir 48 may freely receive exudates when the absorbent member 14 is saturated, the proximal reservoir 48 discourages pooling of the exudates at the periwound area, which might otherwise cause further tissue deterioration and undermine the adhesive bond of the contact layer 12 with the skin "S". Thus, the configuration of the dressing 10 promotes healing of the wound "W".

Figure 6:
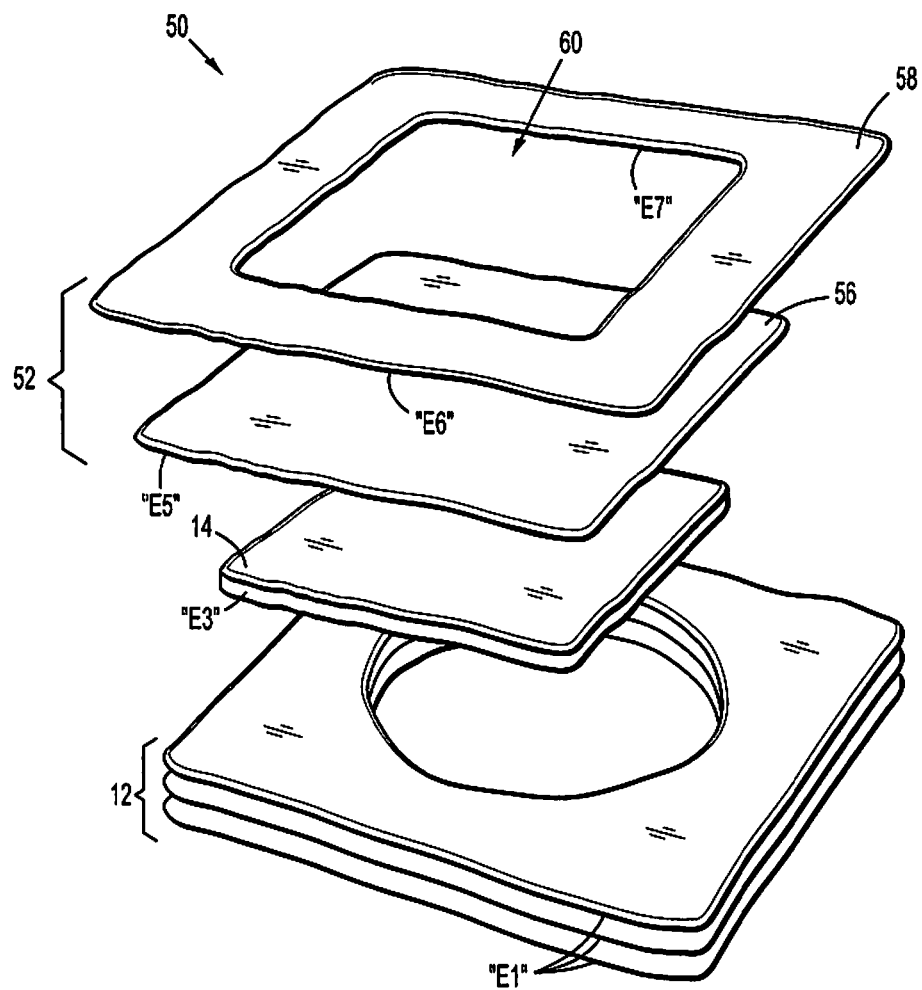
FIG. 6 is an exploded perspective view of an alternate embodiment of a wound dressing including a composite backing layer defining an internal open window in a cover layer thereof in accordance with the present disclosure.

Referring now to FIG. 6, an alternate embodiment of a dressing 50 includes the composite contact layer 12 and the intermediate absorbent member 14 as described above with reference to FIGS. 1 through 6, and also includes a composite backing layer 52. The composite backing layer 52 is constructed of two distinct component layers including a drape layer 56 and a proximal cover layer 58. Both the drape layer 56 and the cover layer 58 may be constructed of a thin film substrate and a patterned adhesive coating 38 in the manner of the backing layer 16 described above. Alternatively, the cover layer 58 may include a continuous coating of the construction adhesive.

The drape layer 56 adheres to the absorbent member 14 such that an outer edge "E5" of the drape layer 56 is coincident with the outer edge "E3" of the absorbent member 14. Alternatively, the drape layer 56 may extend laterally beyond the outer edge "E3" of the absorbent member 14. The cover layer 58 adheres to the drape layer 56 and to the contact layer 12. An outer edge "E6" of the cover layer 58 is coincident with the outer edge "E1" of the composite contact layer 12, and an inner edge "E7" of the cover layer 58 is disposed laterally inward with respect to the outer edge "E5" of the drape layer 56. An internal proximal window 60 is defined in the cover layer 58 such that the proximal window 60 is disposed adjacent the absorbent member 14 when the dressing 50 is assembled.

The composite backing layer 52 provides rigidity to a lateral perimeter of the dressing 50, and thus, may prohibit lateral swelling of the absorbent member 14. The rigidity at the lateral perimeter also aids in maintaining the integrity of the dressing 50 as the absorbent member becomes saturated, and facilitates application of the dressing 50.

Although the foregoing disclosure has been described in some detail by way of illustration and example, for purposes of clarity or understanding, it will be obvious that certain changes and modifications may be practiced within the scope of the appended claims.

What is claimed is:

1. A wound dressing, which comprises:
    a porous contact layer for positioning adjacent a wound, wherein material of the porous contact layer is porous for permitting transmission of wound fluids and moisture vapor there through, the porous contact layer defining a distal wound-facing surface and an opposed proximal surface, the porous contact layer defining a distal window extending there through;
    an absorbent member disposed in superimposed relation to the distal window of the porous contact layer, the absorbent member dimensioned to extend laterally beyond the distal window such that a portion of the absorbent member overlaps and is secured to the proximal surface of the porous contact layer;
    a drape layer disposed on a proximal side of the absorbent member, a distal side of the drape layer adhesively coated to fasten the drape layer to the absorbent member; and
    a cover layer defining a proximal window, the cover layer disposed over the drape layer such that the proximal window is adjacent the absorbent member, a distal side of the cover layer adhesively coated to secure the cover layer to the porous contact layer.

2. The wound dressing according to claim 1, wherein at least about 50% of the surface area of a distal side of the absorbent member is exposed to a distal side of the dressing through the distal window of the porous contact layer.

3. The wound dressing according to claim 2, wherein at least about 85% of the surface area of the distal side of the absorbent member is exposed through the distal window of the porous contact layer.

4. The wound dressing according to claim 3, wherein the absorbent member defines a generally rectangular shape, and wherein the distal window of the porous contact layer defines a generally circular shape.

5. The wound dressing according to claim 4, wherein the absorbent member is constructed of an open-celled polyurethane foam.

6. The wound dressing according to claim 3, wherein the absorbent member defines a generally rectangular shape, and wherein the distal window of the porous contact layer defines a generally oval shape.

7. The wound dressing according to claim 1, wherein the porous contact layer includes a plurality of perforations exhibiting a diameter in a range of 200 to 1000 microns and spaced such that the porous contact layer exhibits a perforation density in a range of 50 to 300 perforations per square inch.

8. The wound dressing according to claim 7, wherein the perforations exhibit a diameter of 500 microns, and wherein the perforation density of the porous contact layer is 85 microns per square inch.

9. The wound dressing according to claim 7, wherein the porous contact layer is constructed as a composite including a thin film substrate component coated on a distal side with a pressure sensitive, wound-side adhesive component, and coated on a proximal side with a construction adhesive component, the plurality of perforations extending through each of the thin film substrate component, the pressure sensitive, wound-side adhesive component, and the construction adhesive component in substantial alignment.

10. The wound dressing according to claim 1, wherein the porous contact layer includes a layer of a cross linked, acrylic-based construction adhesive on a proximal side thereof, the cross linked, acrylic-based construction adhesive adhering the absorbent member to the porous contact layer.

11. The wound dressing according to claim 10, wherein the distal side of the drape layer is adhesively coated with a patterned coating of the cross linked, acrylic-based construction adhesive.

12. The wound dressing according to claim 1, wherein at least 50% of the surface area of a distal side of the absorbent member is exposed to a distal side of the dressing through the distal window of the porous contact layer.

13. A wound dressing, which comprises:
    an absorbent member defining a distal wound-facing surface and an opposed proximal surface, the distal wound facing surface defining a surface area;
    a porous contact layer defining a distal window extending therethrough, the porous contact layer including a thin film membrane having a pressure sensitive, wound-side adhesive on a distal side thereof and a continuous coating of a construction adhesive on a proximal side thereof, and wherein the proximal side of the porous contact layer is adhered to the distal wound facing surface of the absorbent member such that at least about 50 percent of the surface area of the distal side of the absorbent member is exposed to a distal side of the wound dressing through the distal window; and
    a backing layer including a patterned coating of the construction adhesive on a distal side thereof, the backing layer adhered to the proximal side of the absorbent member by the patterned coating of the construction adhesive, the construction adhesive configured to permit separation of the backing layer from the absorbent member upon swelling of the absorbent member.

14. The wound dressing according to claim 13, wherein the patterned coating of the construction adhesive is in a range of 0.4 to 0.6 grams of adhesive per 100 square inches of surface area of the backing layer.

15. The wound dressing according to claim 14, wherein the backing layer is constructed as a composite including a drape layer adhered to the absorbent member by the patterned coating of the construction adhesive on a distal side thereof, and a cover layer defining a proximal window, the cover layer adhered to a proximal side of the drape layer by a coating of the construction adhesive.

16. The wound dressing according to claim 14, wherein the cover layer is adhered to a proximal side of the drape layer by a patterned coating of the construction adhesive.

17. The wound dressing according to claim 14, wherein the cover layer is adhered to a proximal side of the drape layer by a continuous coating of the construction adhesive.

18. The wound dressing according to claim 14, wherein an outer edge of the cover layer is coincident with an outer edge of the porous contact layer and an outer edge of the drape layer is coincident with an outer edge of the absorbent member.

19. The wound dressing according to claim 13, wherein the absorbent member is constrained between the backing layer and the porous contact layer such that upon swelling the absorbent member migrates primarily in a distal direction through the distal window of the porous contact layer.

20. The wound dressing according to claim 13, wherein at least 50 percent of the surface area of the distal side of the absorbent member is exposed to a distal side of the wound dressing through the distal window.

\* \* \* \* \*